United States Patent [19]
Miller, Jr. et al.

[11] 3,991,767
[45] Nov. 16, 1976

[54] TUBULAR UNIT WITH VESSEL ENGAGING CUFF STRUCTURE

[75] Inventors: George E. Miller, Jr., Scramento; Paul Kahn, San Francisco; William C. Dabney, Oakland, all of Calif.

[73] Assignee: Cutter Laboratories Inc., Berkeley, Calif.

[22] Filed: Mar. 6, 1975

[21] Appl. No.: 556,185

Related U.S. Application Data

[62] Division of Ser. No. 412,355, Nov. 2, 1973, Pat. No. 3,889,685.

[52] U.S. Cl. ............................ 128/348; 128/349 B; 128/334 R
[51] Int. Cl.² ........................................ A61M 25/00
[58] Field of Search ........... 128/348, 349 B, 349 BV, 128/350 R, 351, 344, 325, 245, 246, 334

[56] References Cited
UNITED STATES PATENTS

| | | | |
|---|---|---|---|
| 2,548,602 | 4/1951 | Greenburg | 128/349 B |
| 3,435,824 | 4/1969 | Gamponia | 128/349 B X |
| 3,435,826 | 4/1969 | Fogarty | 128/348 |
| 3,516,408 | 6/1970 | Montanti | 128/348 X |
| 3,640,282 | 2/1972 | Kamen et al. | 128/349 B X |
| 3,709,227 | 1/1973 | Hayward | 128/351 |
| 3,799,173 | 3/1974 | Kamen | 128/349 B X |
| 3,834,394 | 9/1974 | Hunter et al. | 128/348 |
| 3,850,176 | 11/1974 | Gottschalk | 128/325 |

Primary Examiner—Dalton L. Truluck
Attorney, Agent, or Firm—Gardiner, Sixbey, Bradford & Carlson

[57] ABSTRACT

The tubular unit with vessel engaging cuff structure is a unitary unit including a tube having a compressible cuff surrounding the outer surface thereof. The cuff includes a resilient, porous inner material surrounding the tube and an outer liquid impervious layer which may be bonded to or integrally formed with the inner material. The tube may include means to evacuate fluid from the cuff or, alternatively, separate means are directly connected to the cuff to accomplish such evacuation and contraction of the cuff. Vessel engaging appendages may be incorporated on the cuff.

12 Claims, 4 Drawing Figures

TUBULAR UNIT WITH VESSEL ENGAGING CUFF STRUCTURE

This application is a divisional application of Ser. No. 412,355 filed Nov. 2, 1973, now U.S. Pat. No. 3,889,685.

BACKGROUND OF THE INVENTION

The present invention relates to novel devices for effective operation within a blood vessel or other tubular structure of the body involved in the conveyance of a liquid which effectively operates to occlude a space between the inner walls of the vessel and the outer surface of a catheter or similar substantially tubular instrument. Such devices are useful in any liquid conducting vessel of the body such as blood vessels, urinary tracts, the esophagus or the intestine.

There have been developed a number of catheters for embolectomy or thrombectomy which include an inflatable balloon section or other assemblies adapted for positive expansion into engagement with the inner walls of a blood vessel. Such catheters are disclosed in U.S. Pat. Nos. 3,435,826, 3,467,101, 3,467,102 and 3,472,230 to T. J. Fogarty and in U.S. Pat. No. 3,635,223 to C. H. Klieman. These devices are inserted in a deflated or contracted condition into a blood vessel and subsequently inflated under the influence of positive pressure to expand a section thereof into engagement with the inner walls of the blood vessel. This application of a positive pressure to the walls of the blood vessel is often injurious to tissue causing resultant irritation and also can distort the vessel wall and result in the breaking off of arterial plaque or other deposits. It is virtually impossible to control with any degree of accuracy the size of the balloon portion of a balloon catheter which is inflated by positive pressure once the catheter is inserted within a blood vessel, and over inflation may result in serious damage to the vessel. The same may be true of other devices having sections which are positively expanded such as the Arterial Bypass disclosed in U.S. Pat. No. 3,516,408 to V. L. Montanti.

In tracheal tubes employing an expanded balloon cuff, attempts have been made to eliminate irritation or damage to the trachea caused by balloon cuffs which have been expanded in response to positive pressure. As an alternative, cuffs for tracheal tubes have been formed with an elastic cover which is filled with a sponge-like resilient material. This resilient material may be collapsed in response to a vacuum, and to prevent wrinkles in the cuff, the liner or outer surface thereof is formed of elastic material such as latex rubber. A cuff of this type for a tracheal tube is disclosed in U.S. Pat. No. 3,640,282 to J. M. Kamen.

The tracheal tube cuffs having a filling of resilient material which are known to the prior art are intended to provide a substantially air tight seal in the trachea, but such cuffs would have inherent disadvantages if they were to be used in blood vessels. In the sealing of blood vessels, a sealing cuff must provide a liquid tight seal with the vessel wall, and normally the seal will be subjected to liquid pressure. Therefore, in many instances the outside diameter of the cuff member in its normally expanded form should be slightly larger than the inside diameter of the surrounding vessel in the area where the cuff is positioned. In these instances, there should be a slight but untraumatizing pressure exerted by the cuff against the interior vessel walls.

In cases where positive pressures extended into the cuff might result in vessel injury if not carefully controlled, it is preferable to form the outer surface of the cuff integral with or bonded to the filler material within the cuff so that no space can be formed between the two. Such spaces present a low resistance to fluid pressure and result in pockets between the filler material and the outer surface which might result in excessive pressure being applied to some portions of the vessel wall. Also, by bonding the filler material to the outer surface of the cuff, the expansion of the cuff can be limited by the expansion of the filler material and thus closely controlled. This unitary construction is useful but not essential in devices for removing thrombi.

It is the primary object of the present invention to provide a novel and improved tubular unit with vessel engaging cuff structure for the use within liquid conveying vessels of the body. The cuff structure includes an outer vessel engaging surface which may be bonded or otherwise integrally formed with an inner filler material having a number of fluid receiving interstices formed therein. The withdrawal of fluid from this inner filler material causes the outer surface of the cuff structure and the filler material to contract when fluid is withdrawn from the interstices thereof and to expand when fluid is readmitted.

Another object of the present invention is to provide a novel and improved tubular unit with vessel engaging cuff structure for use within liquid conveying vessels of the body wherein the outer cuff configuration may be formed to a particular shape and a cuff is constructed to always return to this expanded shape when unrestrained. The cuff may be formed so as to prevent expansion under pressure beyond the confines of the preformed cuff shape.

A still further object of the present invention is to provide a novel and improved tubular unit with vessel engaging cuff structure for use within liquid conveying vessels of the body wherein engagement of the outer surface of the cuff structure with a vessel wall is accomplished by the normal expansion of an internal filler material to a predetermined shape when fluid previously withdrawn therefrom is reintroduced. The expansion and contraction of this filler material is also employed to some extent to control the contact between the vessel wall and other wall contacting devices formed integral with the outer layer of the vessel engaging cuff structure.

These and other objects of the present invention will readily be apparent upon consideration of the following specification and claims taken in conjunction with the accompanying drawings in which:

Figure 1:
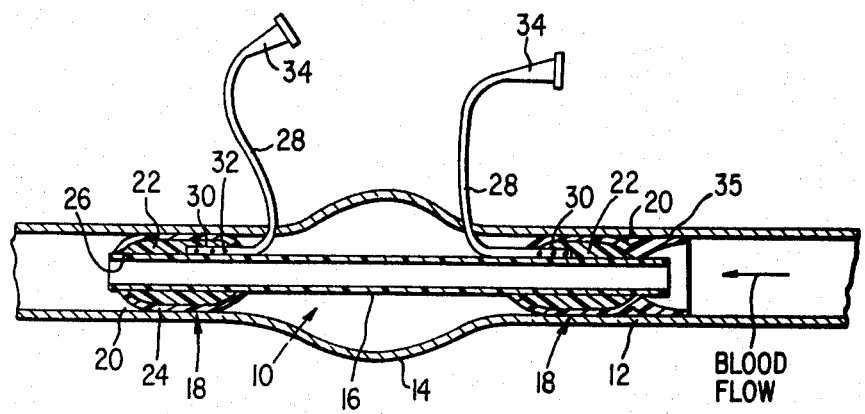
FIG. 1 is a sectional view of the tubular unit with vessel engaging cuff structure of the present invention for use in the repair of an aneurism.

Referring now to FIG. 1, it will be noted that a tubular unit with a vessel engaging cuff structure which is indicated generally at 10 is positioned within the blood vessel 12 for use in the repair of an aneurism 14 in the wall of the blood vessel. Aneurisms can occur anywhere in the arterial system of the body and the most dangerous and difficult to repair are those in the major vessels such as the aorta or the iliac artery. The unit 10 in FIG. 1 may be used in those cases where the aneurism is susceptible to repair rather than replacement. It will be noted that the unit 10 includes an open ended tube 16 which is preferably formed of flexible material compatible with blood. For example, the tube 16 may be formed of silicone rubber, polyethylene, polypropylene, polyurethane, polyvinyl chloride or the like. Mounted upon the tube 16 are spaced cuffs 18 which are positioned to engage the walls of the blood vessel 12 on either side of the aneurism 14. The cuffs 18 are of identical structure, and each has a generally cylindrical shape, although other vessel wall engaging shapes may also be achieved with the cuff structure of the present invention. Each cuff includes an outer surface layer 20 which is impervious to gases or liquids and a resilient sponge-like, reticulated filler material 22 which fills the space between the tube 16 and the surface layer 20. The filler material 22 includes pores or voids which are interconnected so that any fluid, be it gaseous or liquid, can be made to flow into or from the pores. Some of the material suitable for this reticulated structure are polyurethane, slicone elastomer, rubber and polyvinyl alcohol and other similar foamed plastic materials. The same materials may be employed to form the outer surface layer 20, but the outer surface layer will not contain pores or voids. It is preferred that the outer surface layer be unitary with the filler material 22, and this may be achieved by bonding the outer surface layer to the filler material along the adjoining surface 24 therebetween. The outer surface layer may be adhered to the filler material by use of adhesive, but ideally the outer surface is formed by spraying or spreading surface material over the outer surface of the filler material. This causes the outer surface material to extend into some of the pores in the filler material, thereby enhancing the bond. Also, the outer surface layer 20 may be formed integrally at the time the spongy filler material is formed so that an impervious skin is generated over the spongy material. Known molding methods may be employed to form this outer skin surface during the molding of the filler material.

The filler material 22 may be bonded to the tube 16 along the extent of the surface 26 therebetween. Thus the portions of the cuff 18 including the outer surface layer 20 and the filler material 22 form a unitary unit with the tube 16. By providing such a unitary unit, there is no space between the tube 16 and the filler material 22 or between the filler material 22 and the outer surface 20 in which fluid can collect, and fluid may only flow through the pores in the filler material.

To facilitate the introduction and withdrawal of fluid from the interior of the cuff 18, each cuff is provided with a control conduit 28. The control conduit is a small diameter flexible tube having an end portion 30 which extends through the outer surface 20 of the cuff into the filler material 22. The outer surface of the cuff is sealed to the control conduit so that no fluid may escape from the interior of the cuff at the point of entry of the control conduit. Preferably, the end 30 of each control conduit within the cuff is perforated at several points 32 to provide enhanced communication with the fluid within the pores of the filler material 22.

The outer end of each control conduit 28 is provided with a connector 34 which is adapted to connect the control conduit to a suction system. For example, each connector 34 may be a female Luer connector into which the Luer tip of a syringe may be placed. In FIG. 1, the tubular unit with vessel engaging cuff structure 10 is shown with separate connectors 34 on the ends of two separate control conduits 28. It is obvious, however, that the two control conduits might merge at a single outlet having a single connector 34 which would be connected to a suction system for simultaneously withdrawing fluid from both cuffs of the unit.

In using the tubular unit with vessel engaging cuff structure 10 of FIG. 1 in the repair of the aneurism 14, clamps are applied upstream and downstream from the aneurism at points where the artery appears healthy. A slit is then made in the arterial wall at the site of the aneurism 14, and sufficient fluid is withdrawn from cuffs 18 by suction to cause cuff contraction. This may be accomplished by syringes attached to the connectors 34 which operate through the control conduits 28 to withdraw fluid from the interstices of the filler material 22. This withdrawal of fluid causes the sponge like filler material to contract due to the exterior atmospheric or liquid pressure which presses against the outer surface layer 24 of the cuff and is sufficient to overcome the force of elasticity of the filler material. The resultant contraction of the cuff permits the unit 10 to be easily inserted through the slit in aneurism 14 and positioned within the artery with a cuff on either side of the aneurism. Fluid is now permitted to flow back through the control conduits 28 into the interstices of the filler material 22, so that the cuffs return toward normal size and engage the inner walls of the artery. Since positive fluid pressure is normally not supplied through the conduits 28, the normal expansion of the resilient, sponge like filler material 22 causes each cuff to provide a seal which is less injurious to the tissues of the artery. In fact, in some instances, it is preferable to form the outer surface layer 20 of flexible but inelastic material so that the expansion of the cuff 18 will be limited even if positive pressure is inadvertently applied through the control conduit 28. With an inelastic surface, the cuff will expand from a contracted configuration back to a normal expanded configuration, and at this point, further expansion will be prevented by the inelastic outer surface 20 even if positive pressure is applied to the filler material 22.

Once the tubular unit with vessel engaging cuff structure 10 is in place within the artery 12 and the cuffs 18 are expanded against the artery wall, the clamps previously placed on the artery are released so that blood flows freely through the tube 16. Circulation within the artery now remains uninterrupted while the surgeon conducts the necessary repair of the weakened wall of the artery. After the repair is completed, clamps are again applied to the artery, the cuffs 18 are contracted, and the unit 10 is withdrawn through the small remaining slit in the arterial wall. The slit is then sutured and the clamps are released.

Figure 2:
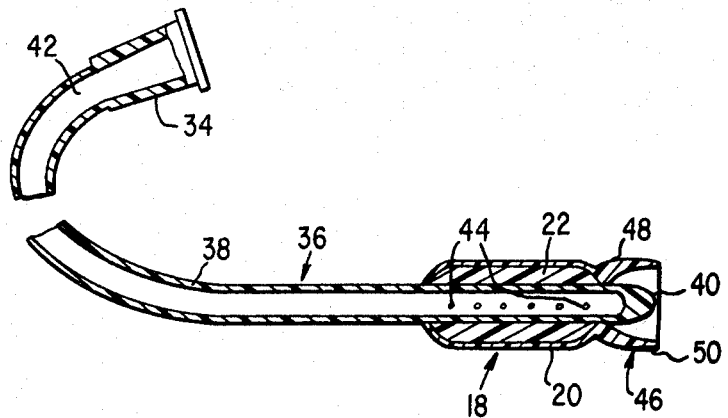
FIG. 2 is a sectional view of a second embodiment of the tubular unit with vessel engaging cuff structure of the present invention for the use as an occluder in the resection of an artery.
Figure 3:
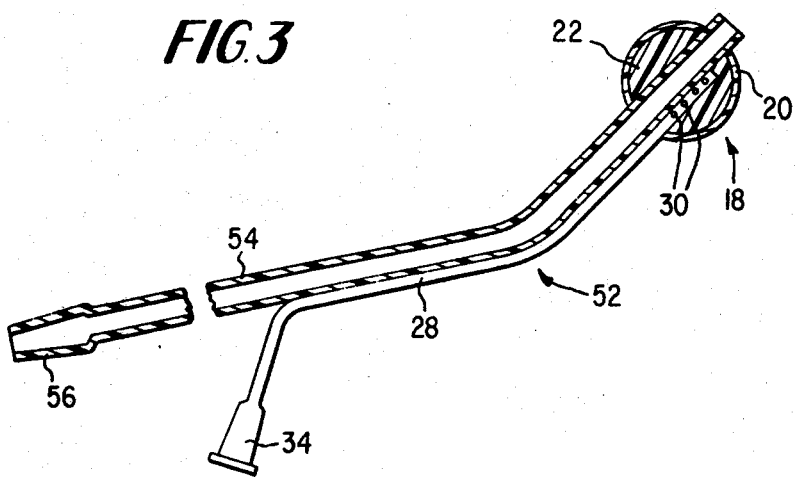
FIG. 3 is a sectional view of a third embodiment of the tubular unit with vessel engaging cuff structure of the present invention for use as a coronary catheter with retaining cuff.
Figure 4:
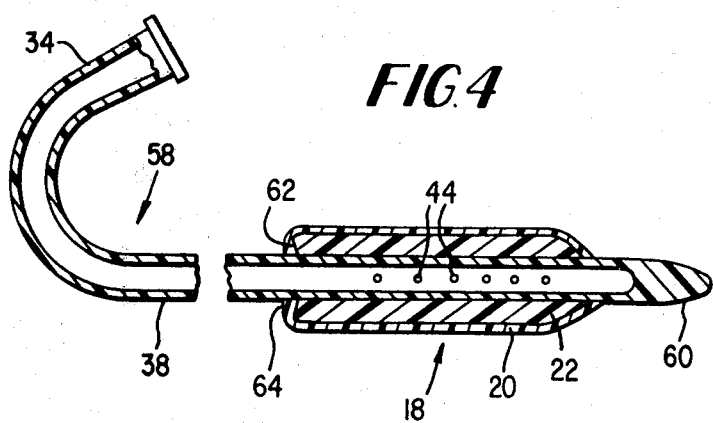
FIG. 4 is a sectional view of a fourth embodiment of a tubular unit with vessel engaging cuff structure of the present invention adapted for use in thromboembolectomy.

FIGS. 2–4 disclose other embodiments of the tubular unit with vessel engaging cuff structure of the present invention, and in these embodiments, the cuff structure is generally identical to that disclosed at 18 in FIG. 1.

Therefore, the reference numerals of FIG. 1 will be applied to corresponding structures found in FIGS. 2–4.

Referring to FIG. 2, there is disclosed an occluder 36 for use during the resection of an artery and the replacement of a damaged section with an arterial graft. There are situations where a damaged artery must be resected and an arterial graft installed to replace the resected portion. For example, an aneurism usually is not susceptible to repair so that the damaged artery must be resected and an arterial graft installed to replace the resected portion, or a coarctation may occur which requires resection and an arterial graft replacement. To install a replacement, the surgeon must have resected ends to work with unencumbered with any device, and therefore the occluder 36 of FIG. 2 becomes necessary. This occluder consists of a tube or conduit 38 having a closed end 40 and an open end 42. A suitable connector, such as the connector 34 of FIG. 1, may be attached to the open end 42 so that suction may be applied to the tube 36.

The closed end 40 of the tube 46 is preferably rounded to provide an insertion tip and a cuff 18 is bonded to the tube adjacent the closed end thereof. This cuff is identical in construction to the cuff of FIG. 1, but in the occluder 36, the tube 38 is provided with apertures or perforations 44 which communicate with the filler material 22 within the cuff. Thus contraction of the cuff may be accomplished by attaching the suction device to the connector 34 and drawing fluid from the filler material 22 through the apertures 44.

To use the occluder 36, the artery is clamped in an area of healthy tissue upstream of the damaged section. A slit large enough to accommodate the occluder is made adjacent to and downstream from the area of the vessel to be resected. The cuff 18 of the occluder is contracted so that the occluder may be introduced into the artery downstream from the slit, and the cuff is then allowed to return toward its original size to engage the arterial wall. The damaged portion of the artery is then resected. Optionally, a second occluder may be inserted into the artery at the resected end near the clamp, and the clamp removed.

Referring again to FIG. 2, the second occluder preferably will include an umbrella like appendage 46 which is attached at the end of the cuff 18 adjacent to the closed end 40 thereof. This appendage is somewhat cup shaped in configuration with the base portion thereof attached to the outer layer 20 at the curved end of the cuff 18, and with the open edge portion extending forwardly of the closed end of the tube 38. The base wall 48 of this appendage is quite thick with relation to the terminal edge of the side wall 50 thereof which is extremely thin. The appendage 46 is formed of flexible material, and therefore the side wall 50, particularly in the area adjacent the outer edge forward of the closed end of the tube, is extremely flexible. The diameter of the appendage may be approximately the same as the diameter of the cuff in the expanded position, and the attachment of the appendage to the outer layer 20 of the cuff insures that the appendage will collapse with the cuff and not impede the insertion of the occluder into a vessel.

When the second occluder is inserted into the artery, the pressures against the second occluder in certain procedures may reach as much as 250 to 350 mm Hg., and at the height of pulsation, the arterial wall may expand sufficiently to cause blood to creep around the cuff of the occluder. The elastic appendage 46 is designed to prevent such blood seepage, for the blood pushes against the appendage and forces the thin side wall 50 thereof into contact with the arterial wall. This reduces the blood pressure on the cuff 18 and prevents seepage between the cuff and the arterial wall. Obviously, the thin sidewall of the appendage facilitates insertion and withdrawal of the appendage without damage to the arterial wall, particularly since the terminal edge thereof is extremely thin and flexible.

The arterial graft is sutured to the resected ends of the vessel except for about a quarter to one half inch at the point where the open ends of the tubes 38 of each occluder protrude. At this point, a loose stitch, such as a purse string stitch is made, and then each occluder cuff 18 is in turn contracted, the occluder is withdrawn, and the loose stitch is tightened and tied to complete the arterial graft.

The use of the occluder 36 is superior to the previously known techniques of clamping off an artery with a vascular clamp, for the occluder is less injurious to the arterial tissue. Similar techniques are also used in the repair of venous blood vessels.

An appendage having a construction similar to that of the appendage 46 may also be used with the tubular unit 10 of FIG. 1 as indicated at 35. The appendage 35 is identical to the appendage 46 with the exception that the closed end 40 is not provided on the tube 16.

FIG. 3 discloses a coronary catheter with retaining cuff indicated generally at 52 for use in open heart surgery. In open heart surgery there frequently is a need to supply blood to the heart muscle via the coronaries to prevent the heart muscle from dying. A coronary catheter for this purpose preferably should have an angled extremity to fit the coronary vessel and be removed from the operating site, and thus the coronary catheter 52 includes an angled, open ended tube 54. This tube is flexible and shaped adjacent one open end thereof to provide a hook-like configuration. A cuff 18 is secured to the tube near the angled portion thereof. This cuff is formed identically to the cuffs of FIGS. 1 and 2 with the exception that the cuff is preferably spherical or ovate and is shorter in length. Also, the cuff 18 of the coronary catheter should be somewhat softer and more resilient than the cuff 18 in FIGS. 1 and 2, but basically, the coronary catheter 52 constitutes one half of the unit 10 of FIG. 1. The open end of the coronary catheter opposite to the cuff is provided with a connection 56 connectable to a blood supply which is to be pumped into the coronary artery into which the catheter has been secured.

A catheter 58 for use in thromboembolectomy is disclosed in FIG. 4. This catheter is similar to the occluder of FIG. 2 and includes tube 38 having a connector 34 at the open end thereof and perforations 44 for communication with the interior of the cuff 18. The closed end of the catheter 58 includes a forward tip 60 which is somewhat firmer than the closed forward end 40 of the catheter 36, for the tip 60 assists in the penetration of a thrombus. Also, it will be noted that the outer layer 20 of the cuff 18 is thickened at 62 to provide a stiffened rear wall 64 on the cuff. This rear wall does not have a round surface similar to that of the front wall of the cuff which is inclined with respect to the surface of the tube 38, but instead has a relatively flat surface which extends outwardly from the surface of the cuff. This rear wall 64 is stiff enough due to the thickened portion 62 of the outer layer 20 to act as a retaining wall for the thrombus as the catheter and cuff are drawn backward through the vessel after penetration of the thrombus. Thus the thrombus will be prevented from slipping around the cuff as it is withdrawn. Since only the rear wall of the cuff is thickened for added stiffness, the remainder of the outer layer 20 which contacts the vessel wall is yielding and flexible so that the cuff will not scrape against plaque adhering to the vessel wall. To insure that plaque will not be engaged and torn from the vessel wall during withdrawal of the cuff, the rear wall 64 is thick adjacent the tube 38 and tapers upwardly so that the outer extremities of the rear wall are thinner and much more flexible than the portions adjacent the tube.

In the use of the device 58 of FIG. 4, an artery or vein is entered above or below a thrombus by means of an incision. Suction is applied to the connector 34 to remove fluid through the perforations 44, thereby constricting the filler material 22 and the outer surface 20 bonded thereto. The catheter 58 with the constricted cuff 18 is then introduced through the slit into the blood vessel. Once the cuff section has passed through the thrombus, the cuff is then allowed to return to normal size. Device 58 is withdrawn, and the cuff retains the thrombus and carries it forward to the exit slit. After the removal of the thrombus and the device 58, the slit is sutured. It should be noted that the cuff section exerts little or no pressure on the vessel wall, only that which results from the natural return of these structures from a contracted state.

For use in blood vessels, it is generally more advantageous to fill the interstices of the filler material 22 of the cuff 18 with liquid, such as water, since the liquid is less compressible than gas and the volume of the cuff will be less subject to change. However, air or other gas can be used to fill the interstices, particularly when the outer surface 20 of the cuff is formed of flexible but nonelastic material to positively limit cuff expansion.

It will be readily apparent to those skilled in the art that the present invention provides a novel tubular unit with vessel engaging cuff structure which is particularly well adapted for use in the liquid conveying vessels of the body. This device is readily adaptable for uses other than those specifically described, and for example may be employed as a sail to carry a pressure sensor to a desired position in the cardiovascular system. For this use, the device of FIG. 2, without the appendage 46, may be attached to a pressure sensor. The cuff 18 can then be expanded as a sail to carry the sensor into the cardiovascular system, and the size of the cuff in the expanded position would be less than the diameter of the walls of the blood vessel through which it is traveling.

We claim:

1. A tubular unit with vessel engaging cuff structure for use within liquid conveying vessels of the body comprising a tube having at least one open end, at least one compressible cuff surrounding said tube and mounted on said tube, said cuff including a resilient, reticulated filler material having a network of fluid receiving interstices and a vessel engaging, flexible outer surface layer enclosing said filler material, said outer surface layer being formed of a material which is impervious to liquids and gasses, conducting means communicating with said filler material to facilitate the withdrawal of fluid therefrom to contract said cuff inwardly toward said tube from a normal expanded configuration assumed by said cuff when said fluid receiving interstices are filled with fluid, and vessel wall engaging means adapted to engage a vessel wall at a point spaced from the area of engagement of said cuff with the vessel wall, said vessel wall engaging means being mounted on said cuff adjacent one end thereof and being formed integrally with said cuff for contraction by said cuff when said cuff is contracted.

2. A tubular unit with vessel engaging cuff structure for use within liquid conveying vessels of the body comprising a tube having at least one open end, at least one compressible cuff surrounding said tube and mounted on said tube, said cuff including a resilient, reticulated filler material having a network of fluid receiving interstices and a vessel engaging, flexible outer surface layer enclosing said filler material, said outer surface layer being formed of a material which is impervious to liquids and gasses, conducting means communicating with said filler material to facilitate the withdrawal of fluid therefrom to contract said cuff inwardly toward said tube from a normal expanded configuration assumed by said cuff when said fluid receiving interstices are filled with fluid, and vessel wall engaging means mounted upon the outer surface layer of said cuff at the end thereof adjacent one end of the tube, said vessel wall engaging means including a cup-shaped unit of flexible material having a base portion secured to said cuff and an annular sidewall extending from said base portion in spaced relation to said tube, said annular sidewall terminating at a substantially annular terminal edge spaced from said base portion in the direction of the end of said tube.

3. The tubular unit of claim 2 wherein said annular sidewall decreases in thickness from said base portion to said annular terminal edge, said sidewall being of greatly reduced cross-section and having substantial flexibility adjacent said annular terminal edge.

4. The tubular unit of claim 3 wherein said flexible outer surface layer of said cuff is connected to said filler material to form a unitary cuff structure.

5. The tubular unit of claim 2 wherein said tube includes an open end and a closed end, said cuff being mounted on said tube adjacent the closed end thereof.

6. The tubular unit of claim 5 wherein connector means are mounted on the open end of said tube to connect said tube to a suction source, said conducting means including at least one aperture formed in the wall of said tube to connect the interior of said tube with said filler material.

7. The tubular unit of claim 2 wherin said vessel engaging outer surface layer is inelastic to prevent expansion of said cuff beyond a defined normal expanded configuration.

8. The tubular unit of claim 5 wherein said vessel wall engaging means is mounted upon the outer surface layer of said cuff at the end thereof adjacent the closed end of the tube, said vessel wall engaging means including a cup-shaped unit of flexible material having a base portion secured to the outer surface layer of said cuff and an annular sidewall extending from said base portion in spaced relation to said tube, said annular sidewall terminating at a substantially annular terminal edge spaced from the base portion in the direction of the closed end of said tube and decreasing in thickness from said base portion to said annular terminal edge.

9. The tubular unit of claim 2 wherein said tube is an open ended tube, and two spaced cuffs are mounted upon said tube intermediate the open ends thereof, said vessel wall engaging means being mounted upon one of said cuffs.

10. The tubular unit of claim 9 wherein said conducting means include a control conduit for connecting each said cuff to a source of suction, the control conduit for each cuff including a small diameter flexible tube having one end connected to said filler material and connector means provided on the opposite end thereof for connection with said source of suction.

11. A tubular unit with vessel engaging cuff structure adapted for use within a liquid conveying vessel of the body to divert liquid flow within said vessel through said tubular unit while isolating a section of said vessel from liquid flow comprising an open ended tube, first and second compressible cuffs surrounding said tube and mounted on said tube in spaced relationship between the open ends thereof, each said cuff including a resilient, reticulated filler material having a network of fluid receiving interstices and a vessel engaging flexible outer surface layer enclosing said filler material, said outer surface layer being formed of a material which is impervious to liquids and gasses and conducting means communicating with the filler material of each said cuff to facilitate the withdrawal of fluid therefrom to contract said cuffs inwardly toward said tube from a normal expanded configuration assumed by said cuffs when said fluid received interstices are filled with fluid, and vessel wall engaging means mounted on said first compressible cuff adjacent to one end of said first cuff, said vessel wall engaging means including a cup-shaped unit of flexible material having a base portion secured to said first cuffs for diverting liquid flowing through said liquid conveying vessel of the body away from the walls of said vessel into said tubular unit.

12. The tubular unit of claim 11 wherein said flexible outer surface layer for said cuffs is connected to the filler material therefor, said conducting means including a control conduit for connecting the interior of each cuff to a source of suction, said control conduit including a small diameter flexible tube having one end connected to said filler material within said flexible outer surface layer.

* * * * *

UNITED STATES PATENT OFFICE
CERTIFICATE OF CORRECTION

PATENT NO. : 3,991,767
DATED : November 16, 1976
INVENTOR(S) : George E. Miller, Jr., Paul Kahn & C. Dabney It is certified that error appears in the above-identified patent and that said Letters Patent are hereby corrected as shown below:

In claim 1, column 7, line 66, word "contact"
should read --contract--.

In claim 11, column 10, line 10, word "cuffs"
should read --cuff--.

Signed and Sealed this

First Day of March 1977

[SEAL]

Attest:

RUTH C. MASON
Attesting Officer

C. MARSHALL DANN
Commissioner of Patents and Trademarks